United States Patent [19]

Ivory

[11] 4,298,348

[45] Nov. 3, 1981

[54] TIME-TEMPERATURE INDICATOR COMPOSITION

[75] Inventor: Dawn M. Ivory, Randolph, N.J.

[73] Assignee: Allied Corporation, Morris Township, Morris County, N.J.

[21] Appl. No.: 126,515

[22] Filed: Mar. 3, 1980

[51] Int. Cl.³ ............................................ G01N 21/06
[52] U.S. Cl. ................................. 23/230 R; 116/201; 116/206; 116/207; 422/56
[58] Field of Search ..................... 23/230 R; 422/56; 116/201, 206, 207

[56] References Cited

U.S. PATENT DOCUMENTS

| | | | |
|---|---|---|---|
| 3,923,622 | 12/1975 | Baughman | 204/159.22 |
| 3,999,946 | 12/1976 | Patel et al. | |
| 4,125,534 | 11/1978 | Yee | |
| 4,164,458 | 8/1979 | Patel | |
| 4,189,399 | 2/1980 | Patel | |
| 4,195,055 | 3/1980 | Patel | 422/56 |
| 4,195,056 | 3/1980 | Patel | 422/56 |
| 4,195,057 | 3/1980 | Patel | 422/56 |
| 4,195,058 | 3/1980 | Patel | 422/56 |
| 4,208,186 | 6/1980 | Patel | 422/56 X |
| 4,228,126 | 10/1980 | Patel | 422/56 |

OTHER PUBLICATIONS

V. Enkelmann, Macromol Chem. 179, 2811-2813 (1978).
D. Bloor et al., Proceedings of NATO Advanced Research on Molecular Metals (Les Arcs, France, Sep. 10-16, 1978), pp. 2-5.
J. Mayerle et al., IBM Research Division, San Jose, CA 95193 (undated), The Crystal & Molecular Structure of 2,4-Heyadiyn-1,6 diol-bis.

*Primary Examiner*—Ronald Serwin
*Attorney, Agent, or Firm*—Alan M. Doernberg

[57] ABSTRACT

An improved recording device is described, useful for measuring the integrated time-temperature or integrated radiation-dosage history of an article, comprising a substrate onto which 2,4-hexadiyn-1,6-diol-bis-(p-chlorobenzenesulfonate) is deposited. The inactive form is capable of being converted by melt recrystallization to an active form, which undergoes 1,4-addition polymerization resulting in an irreversible, progressive color change. The color change produced at any given point in time represents an integrated time-temperature history of thermal annealing or integrated radiation-dosage history of exposure to actinic radiation to which an article has been exposed.

Also described is a process for converting an inactive form of 2,4-hexadiyn-1,6-diol-bis(p-chlorobenzenesulfonate) to its active form by thermal recrystallization.

6 Claims, No Drawings

TIME-TEMPERATURE INDICATOR COMPOSITION

DESCRIPTION

BACKGROUND OF THE INVENTION

1. Field of the Invention

This invention relates to an improved device containing an inactive form of an acetylenic compound, having at least two conjugated C≡C groups, for measuring the integrated time-temperature history or integrated radiation-dosage history to which a perishable product has been exposed.

2. Brief Description of the Prior Art

Acetylenic compounds, containing at least two conjugated C≡C groups, being cyclic or acyclic, symmetrical or unsymmetrical, diynes, triynes, tetraynes or hexaynes, and hereinafter referred to a diacetylenes, are an extremely useful class of compounds. They undergo 1,4-addition polymerization in the solid state, upon exposure to thermal annealing or actinic radiation, including ultraviolet and gamma radiation, thereby resulting in highly colored polymers. Utilization of this class of compounds has been described in U.S. Pat. No. 3,923,622 (Baughman and Yee, 1975) for use as cyclically bound ladder polymers; U.S. Pat. No. 3,999,946 (Patel, Preziosi and Baughman, 1976) for use as time-temperature history indicators; U.S. Pat. No. 4,164,458 (Patel, Aug. 14, 1979) for use as crosslinking agents; U.S. Pat. No. 4,125,534 (Yee, Nov. 14, 1978) for use as thermochromic indicating materials and in indicia-display devices; U.S. Pat. No. 4,125,534 (Nov. 14, 1978) as new carbazole-type photoconductors and non-linear optical materials; U.S. application Ser. No. 038,011 (Baughman et al., May 11, 1979), for use in gradient-type recording devices, and U.S. application Ser. No. 817,069 (Patel, July 19, 1977), now U.S. Pat. No. 4,189,399 (Feb. 19, 1980) as new co-crystallized compositions.

As described in U.S. Pat. No. 3,999,946 (Patel et. al., Dec. 28, 1976) and above-referenced U.S. Application Ser. No. 038,011, diacetylenes can be used in indicators wherein exposure of a diacetylene compound, deposited on a substrate, to thermal annealing or actinic radiation will initiate a 1,4-addition polymerization resulting in a color change. The color change produced at any given point in time represents an integrated-image temperature history of thermal annealing or integrated exposure to actinic radiation.

U.S. Pat. No. 3,999,946, (see the sentence bridging columns 7 and 8; column 6, lines 16-19; column 7, lines 50-51) generally describes the preparation of the indictors by coating crystals of an active diacetylene compound onto a substrate which is then responsive to thermal exposure or exposure to actinic radiation. However, the prepared indicators have the disadvantage that they must be stored at low temperatures and protected from actinic radiation prior to use. The step of protecting the formed indicators, at low temperature during storage and shipping to the point of use, greatly increases the cost of production and introduces an element of uncertainty as to the reliability of the final readings of the devices after use.

U.S. Pat. No. 3,999,946 also discloses at col. 6, lines 36-50 that the solvent chosen for application will affect the activity of the acetylenic compound. Two pending applications disclose methods for converting inactive forms of acetylenic compounds to active forms: U.S. patent application Ser. Nos. 854,933 (Patel and Yee, Nov. 25, 1977) and 911,565 (Patel, June 1, 1978), now U.S. Pat. No. 4,195,055 (Mar. 25, 1980)

What is needed is a device containing a form of diacetylene which can be stored at ambient temperatures during and after manufacture, shipped by standard procedures, and which can be applied to an article and activated by simple means just prior to use.

V. Enkelmann, Macromol. Chem. 179, 2811-2813 (1978) discloses that 2,4-hexadiyn-1,6-diol-bis-(p-chlorobenzenesulfonate) can be obtained in a metastable active form which apparently is isomorphous to the monomer structure of 2,4-hexadiyn-1,6-diol-bis(p-toluenesulfonate), which structure was investigated by V. Enkelmann et al. in Anger. Chem. 89, 432 (1977).

D. Bloor et al., in Proceedings of NATO Advanced Research Institute on Molecular Metals (Les Arcs, France, Sept. 10-16 (1978)) disclose that 2,4-hexadiyn-1,6-diol-bis-(p-chlorobenzenesulfonate) is unreactive in solid state polymerization.

J. J. Mayerle et al., in a report distributed by IBM Research Division describe their crystal structure determination of the inactive form of 2,4-hexadiyn-1,-6-diol-bis-(p-chlorobenzenesulfonate). However, the reference does not describe or suggest the use of the inactive forms of diacetylenes in forming an indicator for use as an integrated time-temperature history indicator.

It has been found that 2,4-hexadiyn-1,6-diol-bis-(p-chlorobenzenesulfonate) forms an active modification and exhibits a different X-ray diffraction pattern compared to the conventional inactive form. The inactive form is incapable of undergoing 1,4-addition polymerization upon exposure to gamma radiation at room temperature or thermal annealing below its melting point, whereas the new active form exhibits the desirable characteristics of a time-temperature indicator.

Furthermore, it has been found that the inactive form of 2,4-hexadiyn-1,6-diol-bis(p-chlorobenzenesulfonate) can be coated on a substrate and converted to an active form prior to use by solvent or melt recrystallization processes. Thus, problems associated in storing and shipping the indicator prior to use are eliminated.

SUMMARY OF THE INVENTION

In accordance with this invention there is provided an improved recording device including a substrate having deposited thereon at least one indicator, said indicator comprised of 2,4-hexadiyn-1,6-diol-bis-(p-chlorobenzenesulfonate) being in inactive form. This compound contains two conjugated C≡C groups, capable of undergoing a 1,4-addition polymerization upon thermal annealing or exposure to actinic radiation, thereby undergoing an irreversible, progressive color change, wherein the color produced at any time during the color change represents an integrated time-temperature history of thermal annealing or integrated radiation dosage history of exposure to actinic radiation. 2,4-hexadiyn-1,6-diol-bis(p-chlorobenzenesulfonate) is in an inactive form and should be positioned for exposure to the conditions to be recorded and capable of in situ conversion, by melt or solvent recrystallization, to an active form capable of undergoing 1,4-addition polymerization. The active and inactive forms exhibit different X-ray crystallographic diffraction patterns, and the active form is capable of undergoing 1,4-addition polymerization upon exposure to gamma radiation at room temperature or thermal annealing below its melting point.

Also provided is a process for activating the device of this invention wherein the inactive form is converted to the active form by melt recrystallization comprising heating the inactive form above its melting point.

Further provided is a process for activating the device of this invention wherein the inactive form is converted to the active form by solvent recrystallization comprising contacting the inactive form with a solvent capable of converting the inactive form to an active form.

Further provided is a process for measuring the integrated time-temperature history of thermal annealing or integrated radiation-dosage history of exposure to actinic radiation, to which an article has been subjected, comprising applying the improved device of this invention to an article and converting the inactive form in situ to an active form by melt or solvent recrystallization.

In addition, there is also provided a film and a fiber made from an inactive form of the above compound capable of existing in both active and inactive forms.

DETAILED DESCRIPTION OF THE INVENTION AND PREFERRED EMBODIMENTS

This invention is based upon the discovery that an active form of a 2,4-hexadiyn-1,6-diol-bis(p-chlorobenzenesulfonate) can be prepared from the inactive form by melt or solvent recrystalization. When the inactive form is subjected to gamma radiation at room temperature or thermal annealing below 80° C., it is not converted to an active form. The inactive form can be converted by solvent or melt recrystallization into an active form, which can undergo 1,4-addition polymerization under the above conditions, thus resulting in brightly colored polymer.

By taking advantage of this property, indicators containing an inactive form of 2,4-hexadiyn-1,6-diol-bis(p-chlorobenzenesulfonate) can be manufactured, stored and shipped under normal conditions without special resort to refrigerated and light-protected environments; and can be activated in situ for use when desired.

The active crystalline form of a 2,4-hexadiyn-1,6-diol-bis(p-chlorobenzenesulfonate), exhibits a different X-ray powder crystallographic diffraction pattern than the inactive form and generally has a melting point higher than that of the inactive form. The X-ray data referred to herein are obtained by conventional techniques and melting point behavior is usually determined by a Fisher-Johns melting point apparatus or by differential scanning calorimetry.

In general, the inactive form of a 2,4-hexadiyn-1,6-diol-bis(p-chlorobenzenesulfonate) will be obtained from solution where very rapid precipitation conditions are employed. Typically, rapid precipitation will occur upon rapid cooling of the solution, rapid evaporation of the solvent, or adding the solution to another liquid which is miscible with the solvent, but acts as a non-solvent for the acetylenic compound.

A further subject of the invention is a process for producing an active form of 2,4-hexadiyn-1,6-diol-bis(p-chlorobenzenesulfonate) comprising dissolving a diacetylene in a solvent therefor, and precipitating said compound from the solution at a rate sufficiently slower than the rate of precipitation of an inactive form of the compound so that substantially only the active form is obtained. In general, a solvent or a combination of solvents is chosen such that the diacetylene recrystallizes slowly from the solvent medium. The inactive form of 2,4-hexadiyn-1,6-diol-bis(p-chlorobenzenesulfonate) is obtained when recrystallizing crude material from acetone and allowing the crystallization to occur rapidly; whereas the active form results when the recrystallization is allowed to proceed slowly.

Elemental analyses show that both active and inactive forms have the same compositions. X-ray diffraction studies show that both the inactive and active forms are monoclinic, but differ in the space group and lattice parameters. These findings indicate that the monomer molecule packing in the active form is much closer than in the inactive form, in agreement with the observed polymerization in the solid state.

PREPARATION OF THE INACTIVE FORM

The inactive form of 2,4-hexadiyn-1,6-diol-bis-(p-chlorobenzenesulfonate) can be converted to the active form by heating the inactive form above its melting point, then allowing it to cool to room temperature. For example, the inactive form (colorless needles) of 2,4-hexadiyn-1,6-diol-bis-(p-chlorobenzenesulfonate) is heated to 150° C., and rapidly cooled to 25° C., resulting in an active form as ivory solids. Thermal analysis (DSC) shows a melting transition at about 126° C. during the initial heating of the crystalline inactive form of 2,4-hexadiyn-1,6-diol-bis(p-chlorobenzenesulfonate) from 25° C. to 150° C. at a heating rate of 5° C./min. When the active form of PCBS is heated from 25° C. to 150° C. at a heating rate of 5° C./min, a melting transition at 123° C. is observed.

By heating the inactive form at a temperature up to about 20° C. above its melting point, preferably 5° to 15° C. above its melting point, and allowing to cool to room temperature (25° C.), the active form will generally be obtained. The process of activating an indicator containing 2,4-hexadiyn-1,6-diol-bis(p-chlorobenzenesulfonate) based on a melt recrystallization process, is also a subject of this invention.

The inactive form can also be prepared by spraying a solution of 2,4-hexadiyn-1,6-diol-bis(p-chlorobenzenesulfonate) onto a substrate and allowing the solvent to evaporate rapidly. For example, spraying an acetone or tetrahydrofuran solution of 2,4-hexadiyn-1,6-diol-bis(p-chlorobenzenesulfonate) onto filter paper or aluminum foil, and allowing the solvent to evaporate rapidly, for example, by passing a stream of air over the surface, results in the inactive form.

Methods of preparation of 2,4-hexadiyn-1,6-diol-bis-(p-chlorobenzenesulfonate) applicable in this invention, including starting materials and synthetic procedures, are adequately described in the above-referenced Bloor and Mayerle articles.

One form of the device of this invention comprises a substrate having deposited thereon an indicator composition containing 2,4-hexadiyn-1,6-diol-bis(p-chlorobenzenesulfonate) in an inactive crystalline form, which is converted to an active form by melt recrystallization.

Substrates

The substrate of the device can be any material which does not chemically interfere with device operation and provides sufficient rigid support for the inactive form of the diacetylene compound deposited thereon. Included among representative examples of substrates are filter paper, aluminum foil, plastic, glasses and the like. The back of the substrate, in addition, may also be coated with an adhesive to secure the device to the article being monitored.

The substrate can optionally be covered with a suitable packaging material, such as plastic or polymer film which does not chemically interfere with device operation and which is preferably transparent, allowing for convenient visual inspection of the device during usage. Representative examples of packaging materials are transparent polyethylene, polypropylene, polyethylene terephthalate and the like.

The indicator containing the inactive form of the 2,4-hexadiyn-1,6-diol-bis(p-chlorobenzenesulfonate) may also contain a binder material such as an epoxy glue, lacquer or shellac to adhere the 2,4-hexadiyn-1,6-diol-bis-(p-chlorobenzenesulfonate) crystals into a suitable medium to be placed onto the substrate.

Devices

The device can be suitably activated, prior to use, by placing the device onto the article to be monitored and converting the inactive form to the active form by a blast of hot air, or by hot pressing, followed by rapid cooling to ambient temperature. A convenient method of activation can be supplied with a conventional high wattage, hot air gun, having high temperature and low temperature settings.

Various modifications of the basic device can be made by one skilled in the art without departing from the scope and spirit of the instant invention.

A further embodiment of the device is where the device contains an indicator strip containing an inactive form of 2,4-hexadiyn-1,6-diol-bis(p-chlorobenzenesulfonate) which is activated prior to use by solvent recrystallization. The solvent applicable in this embodiment is one which is capable of converting the inactive form of 2,4-hexadiyn-1,6-bis(p-chlorobenzenesulfonate) to the active form and in general, is chosen from the solvents described above for recrystallizing 2,4-hexadiyn-1,6-diol-bis(p-chlorobenzene-sulfonate). Preferred solvents in this embodiment are acetone, tetrahydrofuran and dioxane.

The composition of the substrate and indicator are the same as discussed above for the melt device.

A process for measuring the integrated time-temperature history of thermal annealing or integrated radiation-dosage history of exposure to actinic radiation, to which an article has been subjected, is also a subject of this invention, and comprises applying the device of this invention to an article and converting the inactive crystalline form to the active crystalline form by melt or solvent recrystallization.

It has been found that by heating the inactive form at its melting point, or slightly above, and drawing the melted material into a film upon slow cooling, the active phase is formed resulting in a film, which is strongly dichroic with high brilliance and controlled desired thickness. The advantage for film growth from the inactive form is that the melt obtained from the inactive form contains only monomer molecules while the melt obtained from the active form by conventional methods contains monomers, dimers, trimers and the like. Consequently, uniform and aligned films of diacetylenes can be obtained from the melts of the inactive form; for example, films made from the inactive form of 2,4-hexadiyn-1,6-diol-bis(p-chlorobenzenesulfonate).

PCBS exhibits high brilliancy and is useful in this form as integrated time-temperature history and integrated radiation-dosage indicators. Other applications for such films include polarizers, and polarizing reflectors.

Thus, another form of this invention is a film made from the inactive form of a 2,4-hexadiyn-1,6-diol-bis(p-chlorobenzenesulfonate).

Alternately, the indicator strip of the device of this invention can be prepared by heating an inactive form of 2,4-hexadiyn-1,6-diol-bis(p-chlorobenzenesulfonate) on a substrate, drawing it into a film and rapidly quenching to room temperature, thereby forming a uniform film of the inactive phase. This provides the production of a very uniform coating of the inactive phase of the 2,4-hexadiyn-1,6-diol-bis(p-chlorobenzenesulfonate) on the substrate.

The following examples are illustrative of the best mode of carrying out the invention and should not be construed as being a limitation on the scope and spirit of the invention.

EXAMPLE 1

1. Active and Inactive Forms

Recrystallization of PCBS from acetone at different evaporation rates yielded two crystal forms of 2,4-hexadiyn-1,6-diol-bis(p-chlorobenzenesulfonate): A, ivory platelets, having a melting point of 124.5° to 125° C., which was inactive towards 1,4-addition polymerization upon exposure to a total of 50 Mrads of gamma radiation; and B, red needles, having a melting point of about 113° C., which evidenced a color change to metallic green-gold upon exposure to a total of 50 Mrads of gamma radiation. A is an inactive form and B is an active form of PCBS.

Elemental analysis of both compounds showed that they both were of the same empirical formula: $C_{14}H_{12}O_6Cl_2S_2$.

Tables 1 and 2 illustrate the X-ray powder diffraction patterns for the inactive form A and the active form B, respectively, showing that they exist in separate and distinct crystalline forms.

TABLE 1

| | | Inactive Form | | | |
|---|---|---|---|---|---|
| $2\theta$ | d-spacing | $I/I_o$ | $2\theta$ | D-spacing | $I/I_o$ |
| 8.00 | 11.051 | 1 | 26.40 | 3.376 | 2 |
| 9.80 | 9.025 | 3 | 27.29 | 3.265 | 3 |
| 13.02 | 6.799 | <1 | 28.10 | 3.175 | 1 |
| 14.50 | 6.109 | <1 | 32.60 | 3.744 | 3 |
| 16.10 | 5.509 | 100 | 33.00 | 3.712 | 2 |
| 18.00 | 4.928 | <1 | 38.20 | 2.354 | 1 |
| 19.51 | 4.550 | 8 | 40.20 | 2.241 | 1 |
| 20.10 | 4.418 | <1 | 41.75 | 2.212 | 0 |
| 20.70 | 4.291 | 3 | 44.50 | 2.034 | 0 |
| 22.0 | 4.040 | 1 | 50.20 | 1.816 | 0 |
| 23.73 | 3.749 | 5 | 50.90 | 1.792 | 0 |
| 24.25 | 3.670 | 4 | 51.20 | 1.783 | 0 |
| 25.50 | 3.493 | 1 | | | |

TABLE 2

| | | Active Form | | | |
|---|---|---|---|---|---|
| $2\theta$ | d-spacing | $I/I_o$ | $2\theta$ | d-spacing | $I/I_o$ |
| 8.10* | 10.915 | 2 | 23.90 | 3.723 | 24 |
| 9.70* | 9.118 | 16 | 24.81 | 3.589 | 24 |
| 13.10 | 6.758 | 17 | 26.40* | 3.376 | 12 |
| 15.98* | 5.546 | 29 | 27.00 | 3.302 | 24 |
| 18.10 | 4.874 | 100 | 28.00 | 3.187 | 26 |
| 19.50* | 4.641 | 11 | 30.20 | 2.959 | 6 |
| 20.40 | 4.353 | 12 | 31.80 | 2.814 | 3 |
| 21.00 | 4.230 | 15 | 32.90 | 2.722 | 3 |
| 21.60* | 4.114 | 11 | 38.50 | 2.338 | 4 |

TABLE 2-continued

| | Active Form | | | | |
|---|---|---|---|---|---|
| 2θ | d-spacing | I/I$_o$ | 2θ | d-spacing | I/I$_o$ |
| 22.40 | 3.969 | 17 | 40.90 | 2.206 | 5 |
| 23.50 | 3.786 | 23 | 43.90 | 2.062 | 4 |
| | | | 44.70* | 2.027 | 5 |

*peaks which could, in part or in whole, be associated with the inactive phase.

2. Conversion

It was found that by heating the inactive ivory platelets at a temperature of about 140° C. a melt was formed, which when allowed to come to room temperature, resulted in the active form B.

EXAMPLE 2

Recrystallizing the above ivory solid A from a 50% hexane/tetrahydrofuran solution at a concentration of 0.0050–010 g/mL, followed by rapid cooling with an ice-water bath, resulted in an inactive form, as colorless, needle-like crystals, melting point 126°–127° C. This form was inactive towards 1,4-addition polymerization upon the application of mechanical stress at 138 MPa (20,000 psi) for several minutes, and upon exposure for several days ultraviolet, visible radiation and about 50 Mrads of gamma radiation (at a dosage rate of about 1 Mrad/hr).

The inactive form, when heated at a temperature of 140°–150° C., followed by allowing to cool to room temperature, was converted to a solid which turned red in color upon standing at room temperature for 15 minutes.

EXAMPLE 3

Solid A (1.6 g) from Example 1 was dissolved in 60 mL of acetone and sprayed onto Whatman No. 1 filter paper. The paper was dried and put through a heat press at about 140° C. When left at room temperature, the paper turned red in about 15 minutes.

I claim:

1. A process for activating a recording device including a substrate having deposited thereon 2,4-hexadiyn-1,6-diol-bis(p-chlorobenzenesulfonate) in an inactive form which comprises heating the device above the melting point of the inactive form and cooling the device to form an active form of 2,4-hexadiyn-1,6-diol-bis(p-chlorobenzenesulfonate).

2. A process for measuring the integrated time-temperature history of thermal annealing or integrated radiation-dosage history of exposure to actinic radiation, to which an article has been subjected, comprising applying to said article an inactive form of 2,4-hexadiyn-1,6-diol-bis(p-chlorobenzenesulfonate) and converting the inactive form in situ to an active form by melt recrystallization.

3. A process of forming an active time-temperature indicator composition which comprises heating the inactive form of 2,4-hexadiyn-1,6-diol-bis-(p-chlorobenzenesulfonate) above its melting point and cooling the melt to form crystals of an active form of 2,4-hexadiyn-1,6-diol-bis(p-chlorobenzenesulfonate).

4. In a combination of a substrate susceptible to adverse effects on exposure to heat or actinic radiation for a measurable period and an acetylenic time-temperature indicator composition, the improvement wherein the acetylenic time-temperature indicator composition is 2,4-hexadiyn-1,6-diol-bis(p-chlorobenzenesulfonate).

5. The combination of claim 4 wherein the 2,4-hexadiyn-1,6-diol-bis(p-chlorobenzenesulfonate) is in an active form.

6. The combination of claim 4 wherein 2,4-hexadiyn-1,6-diol-bis(p-chlorobenzenesulfonate) is in an inactive form activatable by thermal recrystallization.